(12) United States Patent
Kang et al.

(10) Patent No.: US 10,188,808 B2
(45) Date of Patent: Jan. 29, 2019

(54) FIBER OPTIC DISTAL SENSOR CONTROLLED DRUG INJECTOR

(71) Applicant: The Johns Hopkins University, Baltimore, MD (US)

(72) Inventors: Jin U. Kang, Ellicott City, MD (US); Peter L. Gehlbach, Monkton, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 629 days.

(21) Appl. No.: 14/163,491

(22) Filed: Jan. 24, 2014

(65) Prior Publication Data

US 2015/0209527 A1 Jul. 30, 2015

(51) Int. Cl.
*A61M 5/46* (2006.01)
*A61B 5/00* (2006.01)
(Continued)

(52) U.S. Cl.
CPC ............ *A61M 5/46* (2013.01); *A61B 5/0066* (2013.01); *A61B 5/6886* (2013.01);
(Continued)

(58) Field of Classification Search
CPC ............ G01B 9/02091; G01B 9/02087; A61B 3/102; A61B 5/0066; A61B 5/6886;
(Continued)

(56) References Cited

U.S. PATENT DOCUMENTS 5,321,501 A * 6/1994 Swanson ............ A61B 1/00096
250/227.27

6,468,265 B1 10/2002 Evans et al.
(Continued)

FOREIGN PATENT DOCUMENTS

JP 4354601 B2 10/2009
WO WO-2006014392 A1 2/2006
(Continued)

OTHER PUBLICATIONS

Ahmad et al., "Cross-correlation-based image acquisition technique for manually-scanned optical coherence tomography," Opt. Express 17(10), 8125-8136 (2009).
(Continued)

*Primary Examiner* — Nathan R Price
*Assistant Examiner* — Melissa A Snyder
(74) *Attorney, Agent, or Firm* — Venable LLP; Henry J. Daley; Laura G. Remus

(57) ABSTRACT

A motion-compensated injector system includes a handheld tool having a hollow shaft with a distal end for insertion into tissue of a subject. The system also includes an optical coherence tomography-based optical detection system having an optical fiber with a distal end at a fixed distance from the distal end of the hollow shaft, and an optical sensor to receive a signal from the optical fiber. The system further includes an actuator to move the hollow shaft in an axial direction, and a control unit to control the actuator. The optical detection system can monitor a distance between the distal end of the optical fiber and a reference portion of the tissue of the subject, and the control unit can control the actuator to move the hollow shaft to compensate for relative motion between the handheld tool and the portion of the tissue.

24 Claims, 7 Drawing Sheets

(51) Int. Cl.
 A61M 5/172 (2006.01)
 A61M 5/158 (2006.01)
(52) U.S. Cl.
 CPC ... *A61M 5/1723* (2013.01); *A61M 2005/1585* (2013.01); *A61M 2205/3306* (2013.01)
(58) Field of Classification Search
 CPC ....... A61B 34/74; A61B 34/77; A16B 5/0073; A61M 5/46
 See application file for complete search history.

(56) References Cited

U.S. PATENT DOCUMENTS

| | | | |
|---|---|---|---|
| 6,858,003 B2 | 2/2005 | Evans et al. | |
| 7,933,024 B2 | 4/2011 | Hirose | |
| 8,328,725 B2* | 12/2012 | Anthony | A61B 5/6843 600/459 |
| 8,864,655 B2* | 10/2014 | Ramamurthy | A61B 5/06 600/117 |
| 2001/0024320 A1 | 9/2001 | Okada | |
| 2002/0163715 A1 | 11/2002 | Engelhardt et al. | |
| 2004/0171334 A1 | 9/2004 | Turnac et al. | |
| 2005/0029978 A1 | 2/2005 | Oleynikov et al. | |
| 2007/0076217 A1 | 4/2007 | Baker et al. | |
| 2007/0081732 A1 | 4/2007 | Makiyama et al. | |
| 2008/0278781 A1 | 11/2008 | Sander | |
| 2009/0196477 A1 | 8/2009 | Cense et al. | |
| 2009/0253985 A1 | 10/2009 | Shachar et al. | |
| 2010/0191176 A1* | 7/2010 | Ho | A61F 9/007 604/22 |
| 2013/0123759 A1* | 5/2013 | Kang | A61B 17/00 606/1 |
| 2014/0088502 A1* | 3/2014 | Matheny | A61K 31/726 604/121 |

FOREIGN PATENT DOCUMENTS

| | | |
|---|---|---|
| WO | WO-2006077107 A1 | 7/2006 |
| WO | WO-2008091755 A1 | 7/2008 |
| WO | WO-2008137710 A1 | 11/2008 |
| WO | WO-2011091369 A1 | 7/2011 |
| WO | WO-2011115627 A1 | 9/2011 |
| WO | WO-2011139895 A1 | 11/2011 |
| WO | WO-2012/012540 A2 | 1/2012 |
| WO | WO-2012/088320 A2 | 6/2012 |

OTHER PUBLICATIONS

An and R. K. Wang, "In vivo volumetric imaging of vascular perfusion within human retina and choroids with optical microangiography," Opt.Express 16, 15 (2008).
Becker et al., "State estimation and feedforward tremor suppression for a handheld micromanipulator with a Kalman filter," IEEE/RSJ, International Conference on Intelligent Robots and Systems, 5160-6165(2011).
Benalcazar, W. Jung, and S. A. Boppart, "Aberration characterization for the optimal design of high-resolution endoscopic optical coherence tomography catheters," Opt.Lett. 37, 3 (2012).
Boppart et al., "Forward-imaging instruments for optical coherence tomography," Opt. Lett. 22 (21), 1618-1620 (1997).
Boppart et al., "Intraoperative assessment of microsurgery with three-dimensional optical coherence tomography," Radiology, vol. 208, pp. 81-86, 1998.
Boppart et al., "Optical coherence tomography: feasibility for basic research and image-guided surgery of breast cancer," Breast Cancer Res. Treatment 84(2), 85-97(2004).
Chen et al., "Noninvasive imaging of in vivo blood flow velocity using optical Doppler tomography," Opt. Lett. 22(14), 1119-1121(1997).
Chien et al., "12th International Conference on Cochlear Implants and Other Implantable Auditory Technologies," (2012).
Choma et al., "Sensitivity advantage of swept source and Fourier domain optical coherence tomography," Opt.Express 11, 7 (2003).
D. Boer et al., "Improved signal-to-noise ratio in spectral-domain compared with time-domain optical coherence tomography," Opt. Lett, 28, 3 (2003).
Dabbs, "Fiber-optic confocal microscope: FOCON," Appl. Opt. 31(16), 3030 (1992).
Duncan et al., "Processing algorithms for tracking speckle shifts in optical elastography of biological tissues, " J. Biomed. Opt. 6(4), 418-426(2001).
Fercher et al., "Measurement of intraocular distances by backscattering spectral interferometry," Opt. Commun. 17, 6 (1995).
Ford et al., "Fibre imaging bundles for full-field optical coherence tomography," Measurement Science and Technology, 2007, vol. 18, pp. 2949-2957.
Fujimoto, Daniel L. Farkas, Biomedical Optical Imaging, Oxford University Press, Inc. 198 Madison Avenue, New York, New York 10016 (2009).
Goebel et al., "Miniaturized two-photon microscope based on a flexible coherent fiber bundle and a gradient-index lens objective," Opt. Lett. 29, 2521-2523 (2004).
Gmitro, and D. Aziz, "Confocal microscopy through a fiber-optic imaging bundle," Opt. Let. 18, 565(1993).
Ha et al., "Compensation of motion artifacts in catheter-based optical frequency domain imaging," Opt. Express 18(11), 11418-11427 (2010).
Han et al., "Handheld forward-imaging needle endoscope for ophthalmic optical coherence tomography inspection," J. Biomed. Opt. 13(2), 020505(2008).
Han et al., "Pixelation effect removal from fiber bundle probe based optical coherence tomography imaging," Opt. Express. 18, 7427-7439 (2010).
Han et al., "Common path optical coherence tomography with fibre bundle probe," Electron. Lett. 45(22), 1110-1112 (2009).
Hillman et al., "Common approach for compensation of axial motion artifacts in swept-source OCT and dispersion in Fourier-domain OCT," Optics Express, 2012.
Huang et al., "Motion compensated fiber-optic confocal microscope based on a common-path optical coherence tomography distance sensor," Opt. Eng. 50(8), 083201 (2011).
Huang et al., "Noncontact common-path Fourier domain optical coherence tomography method for in vitro intraocular lens power measurement", J. Biomed. Opt. 16(12), 126005(2011).
Huang et al., "Optical coherence tomography," Science, vol. 254, pp. 1178-1181, 1991.
Huang et al., "Real-time 3D and 4D Fourier domain Doppler optical coherence tomography based on dual graphics processing units," Biomed. Opt. Express 3(9), 2162-2174 ( 2012).
Huang et al., "Motion-compensated hand-held common-path Fourier-domain optical coherence tomography probe for image-guided intervention," Biomed. Opt. Express, vol. 3, Iss. 12, pp. 3105-3118 (2012).
Huber et al., "Buffered Fourier domain mode locking: unidirectional swept laser sources for optical coherence tomography imaging at 370,000 lines/s," Opt. Lett., vol. 31, pp. 2975-2977, 2006.
Huo et al., "Forward-viewing resonant fiber-optic scanning endoscope of appropriate scanning speed for 3D OCT imaging," Opt. Express 18(14),14375-14384(2010).
Iftimia et al., "Adaptive ranging for optical coherence tomography," Opt. Express 12(17), 4025-4034 (2004).
International Search Report and Written Opinion issued in International Application No. PCT/US2013/059736 dated Dec. 20, 2013.
International Search Report and Written Opinion issued in PCT Application No. PCT/US2013/053259 dated Aug. 1, 2013.
International Search Report and Written Opinion of PCT/US2012/036643.
International Search Report issued in PCT/US2011/044693 dated Mar. 20, 2012.
Jafri et al., "Optical coherence tomography guided neurosurgical procedures in small rodents," J. Neurosci. Methods 176(2), 85-89 (2009).

(56) References Cited

OTHER PUBLICATIONS

Jung et al. "Three-dimensional optical coherence tomography employing a 2-axis microelectromechanical scanning mirror," IEEE J. Sel. Top. Quantum Electron. 11(4), 806-810(2005).
Kang et al., "Endoscopic functional Fourier domain common path optical coherence tomography for microsurgery," IEEE J. Sel. Top. Quantum Electron. 16(4), 781-792(2010).
Kang et al., "Real-time three-dimensional Fourier-domain optical coherence tomography video image guided microsurgeries," J. Biomed. Opt. 17(8), 081403 (2012).
Kim et al., "Enhancement of common-path fourierdomain optical coherence tomography using active surface tracking algorithm," Transcations of the Korean Institute, 2012 (Abstract).
Kim et al., "Advanced Confocal Microscope Using Single Hollow-Core Photonic Bandgap Fibre Design," IEEE Electron. Lett., vol. 43(11) 608-609(2007).
Kim et al., "Fiber-Optic Confocal Microscopy Using a 1.55 μm Fiber Laser for Multimodal Biophotonics Applications," Journal of Special Topics in Quantum Electronics, vol. 14(1), 82-87(2008).
Klein et al., "Megahertz OCT for ultrawide-field retinal imaging with a 1050nm Fourier domain mode-locked laser," Opt. Express, vol. 19, pp. 3044-3062, 2011.
Knittel et al., "Endoscope-compatible confocal microscope using a gradient index-lens system," Opt. Comm. 188, 267-273 (2001).
Lee et al., "Motion correction for phase-resolved dynamic optical coherence tomography imaging of rodent cerebral cortex," Opt. Express 19(22), 21258-21270 (2012).
Leitgeb et al., "Ultrahigh resolution Fourier domain optical coherence tomography," Opt. Express 12(10), 2156-2165(2004).
Leitgeb et al., "Performance of fourier domain vs. time domain optical coherence tomography," Opt.Express 11, 6 (2003).
Li et al., "Intraluminal fiber-optic Doppler imaging catheter for structural and functional optical coherence tomography," Opt.Lett. 26, 3 (2001).
Liang et al., "Intravascular atherosclerotic imaging with combined fluorescence and optical coherence tomography probe based on a double-clad fiber combiner," J.Biomed. Opt. 17, 3 (2012).
Liang et al., "Fiber confocal reflectance microscope (FCRM) for in-vivo imaging," Opt. Express. 9, 821-830 (2001).
Liu et al., "Optimization of an angled fiber probe for common-path optical coherence tomography," Opt. Letts., vol. 38, Issue 15, pp. 2660-2662 (2013).
Liu et al., "Distortion-free freehand-scanning OCT implemented with real-time scanning speed variance correction," Opt. Express 20(15), 16567-16583 (2012).
Maguluri et al., "Three dimensional tracking for volumetric spectral-domain optical coherence tomography," Opt. Express 15(25), 16808-16817 ( 2007).
Mao et al., "Graded-index fiber lens proposed for ultrasmall probes used in biomedical imaging," Appl. Opt 46, 8 (2008).
Mitragotri, "Current status and future prospects of needle-free liquid jet injectors," Nature Rev. Drug Discov. 5, 6 (2006).
Oh et al., ">400 kHz repetition rate wavelength-swept laser and application to high-speed optical frequency domain imaging," Opt. Lett., vol. 35, pp. 2919-2921, 2010.
Pepperkok, C. Schneider, L. Philipson, and W. Ansorge, "Single cell assay with an automated capillary injection system," Exp.Cell.Res. 17, 8 (1988).
Potsaid et al., "Ultrahigh speed 1050nm swept source / Fourier domain OCT retinal and anterior segment imaging at 100,000 to 400,000 axial scans per second," Opt. Express, vol. 18, pp. 20029-20048, 2010.
Potsaid et al., "Ultrahigh speed Spectral / Fourier domain OCT ophthalmic imaging at 70,000 to 312,500 axial scans per second," Opt. Express, vol. 16, pp. 15149-15169, 2008.
Cucu et al., "Active axial eye motion tracking by extended range, closed loop OPD-locked white light interferometer for combined confocal/en face optical coherence tomography imaging of the human eye fundus in vivo," Proc. of SPIE-OSA Biomedical Optics, SPIE vol. 7372, 73721R (2009).
Singh et al., "Physiological tremor during retinal microsurgery," Proc. 28th Annual Conf. IEEE Eng. Med. Bio. Soc.,171-172(2002).
Song et al., "Fiber-optic OCT sensor guided "SMART" microforceps for microsurgery," Biomedical Optics Express vol. 4, Iss. 7, pp. 1045-1050 (2013).
Song et al., "Ball Lens Fiber Optic Sensor based Smart Handheld Microsurgical Instrument," Proc SPIE. Mar. 20, 2013;8576.
Song et al., "Active Tremor Cancellation by a "Smart" Handheld Vitreoretinal Microsurgical Tool using Swept Source Optical Coherence Tomography," Optics Express, vol. 20, No. 21, pp. 23414-23421, Oct. 2012.
Stifter et al., "Polarisation-sensitive optical coherence tomography for material characterization and testing," Insight-Non-Destructing Testing and Condition Monitoring, 47, 209-212(2005).
Tan et al., "In-fiber common-path optical coherence tomography using a conical-tip fiber," Opt. Express 17(4),2375-2380(2009).
Tearney et al., "Scanning single-mode fiber optic catheter-endoscope for optical coherence tomography," Opt.Lett. 21, 3 (1996).
Tearney et al., "In vivo endoscopic optical biopsy with optical coherence tomography," Science 276, 3 (1997).
Vakhtin et al., "Common-path interferometer for frequency-domain optical coherence tomography," App. Opt. 42(34), 6935-6958 (2003).
Wieser et al., "Multi-Megahertz OCT: High quality 3D imaging at 20 million A-scans and 4.5 GVoxels per second," Opt. Express, vol. 18, pp. 14685-14704, 2010.
Xie et al., "Endoscopic optical coherence tomographic imaging with a CMOS-MEMS micromirror," Sensors and Actuators A, 2003, vol. 103, pp. 237-241.
Xie et al., "Fiber-optic-bundle-based optical coherence tomography," Opt. Lett. 30, 1803-1805 (2005).
Yamanari et al., "Full-range polarization-sensitive swept-source optical coherence tomography by simultaneous transversal and spectral modulation," Opt.Express 18, 17 (2010).
Yamanari et al,, "Fiber-based polarization-sensitive Fourier domain optical coherence tomography using B-scan-oriented polarization modulation method," Opt. Express 14, 6502 (2006).
Yang et al., "Interstitial Doppler optical coherence tomography," Opt. Lett. 30, 3 (2005).
Yun et al., "High-speed optical frequency-domain imaging," Opt. Express 11, 11 (2003).
Zhang et al., "A common-path optical coherence tomography distance-sensor based surface tracking and motion compensation handheld microsurgical tool," Progress in Biomedical Optics and Imaging, 2011.
Zhang et al., "A surface topology for microsurgery guidance and intervention based on common-path optical coherence tomography," IEEE Trans. on Biomed. Eng. 56(9),2318-2321(2009).
Zhang et al., "Common-path low-coherence interferometry fiber-optic sensor guided micro-incision," J. Biomed. Opt. 16(9),095003(2011).
Zhang et al., "Graphics processing unit accelerated non-uniform fast fourier transform for ultrahigh-speed, real-time fourier-domain OCT," Optics Express, vol. 18, pp. 23472-23487.
Zhang et al., "Noninvasive volumetric quality evaluation of post-surgical clear corneal incision via high-resolution Fourier-domain optical coherence tomography," Electron. Lett., 46(22), 1482-1483(2010).
Zhang et al., "Real-time intraoperative 4D full-range FD-OCT based on the dual graphics processing units architecture for microsurgery guidance," Biomed. Opt. Express. 2(4), 764-770 (2011).
Zhang et al., "A Fiber-Optic Nerve Stimulation Probe Integrated with a Precise Common-Path Optical Coherence Tomography Distance Sensor," in OSA CLEO/IQEC 2010, CTuP2. http://www.opticsinfobase.org/abstract.cfrn?URI=CLE0-2010-CTuP2.
Zhang et al., "Real-time 4D signal processing and visualization using graphics processing unit on a regular nonlinear-k Fourier-domain OCT system." Opt. Express, 18(11), 11772-11784 (2010).
Zhang et al., "A Free-Hand Surface Tracking and Motion Compensation Microsurgical Tool System based on Common-path Optical Coherence Tomography Distance Sensor," in Conference on Lasers and Electro-Optics, OSA Technical Digest (CD) (Optical Society of

(56) References Cited

OTHER PUBLICATIONS

America, 2010), paper CTuB6. http://www.opticsinfobase.org/abstract.cfm?uri-CLE0-2010-CTuB6.

Zhao et al., "Single camera sequential scan based polarization sensitive SDOCT for retinal imaging," Opt.Lett. 34, 3 (2009).

Zhao et al., "3D refraction correction and extraction of clinical parameters from spectral domain optical coherence tomography of the cornea," Opt. Express 18, 14 (2010).

Zhao et al., "Sensing and three-dimnesional OCT imaging of the cochlea and temporal bone: image-guided cochlear implantation," Proceediungs of SPIE, Mar. 2013, vol. 8565, pp. 1-7.

Zhao et al., "Sapphire ball lens-based fiber probe for common-path optical coherence tomography and its applications in corneal and retinal imaging," Opt. Lett. 37, 3 (2012).

Zhu et al., "Design and validation of an angle-resolved low-coherence interferometry fiber probe for in vivo clinical measurements of depth-resolved nuclear morphology," J.Biomed. Opt. 16(2011).

Zysk et al. "Optical coherence tomography: a review of clinical development from bench to bedside," J. Biomed. Opt. 12(5), 051403 (2007).

\* cited by examiner

FIBER OPTIC DISTAL SENSOR CONTROLLED DRUG INJECTOR

STATEMENT OF GOVERNMENT SUPPORT

This invention was made with U.S. Government support under Grant No. R01 EY021540, awarded by the National Institutes of Health National Eye Institute. The Government has certain rights in this invention.

TECHNICAL FIELD

The field of the currently claimed embodiments of this invention relates to motion-compensated injector systems and methods of using the same, and more particularly systems and methods using optical coherence tomography with a motion-compensated injector.

BACKGROUND

Optical coherence tomography (OCT) has been viewed as an "optical analogy" of ultrasound sonogram (US) imaging since its invention in early 1990's. Compared to the conventional image-guided interventions (IGI) using modalities such as magnetic resonance imaging (MRI), X-ray computed tomography (CT) and ultrasound (US), OCT has much higher spatial resolution and therefore possesses great potential for applications in a wide range of microsurgeries, such as vitreo-retinal surgery, neurological surgery, otolaryngologic surgery and cochlear implantation. It has recently been demonstrated that OCT can be highly effective in freehand or robotically assisted retinal imaging or cochlear implantation, for example. A single-mode fiber can be lensed with state-of-the-art micro-optics to form a light beam with a spot size around 11 μm to 18 μm in retinal imaging, gastrointestinal endoscopy, coronary artery imaging, and needle-based Doppler OCT. Thus, OCT fiber optic sensing and imaging are becoming powerful tools for non-destructive cross-sectional imaging of biological tissues.

Retinal surgery is one example of microsurgery. In current practice, retinal surgery is performed under an operating microscope with free-hand instrumentation. Human limitations include an inability to clearly view surgical targets, physiological hand tremor, and lack of tactile feedback in tool-to-tissue interactions. In addition, tool limitations, such as lack of proximity sensing or smart functions, are important factors that contribute to surgical risk and reduce the likelihood of achieving surgical goals. Current instruments do not provide physiological or even basic interpretive information. Surgical outcomes (both success and failure) are limited, in part, by technical hurdles that cannot be overcome by conventional instrumentation.

An injector is a device that may be used by a surgeon, for example, to deliver small volumes of drug, solutions, or other materials into biological tissues or cells. Examples of injection include delivering of various drugs to biological tissues including, but not limited to, those as delicate and fragile as retina or as robust as heart muscle. In many circumstances, it is more convenient to use a simple hand-held injector for injection and/or a manually-scanned probe for obtaining OCT images of tissues and organs which might otherwise be inaccessible using standard mechanical scanning heads. A hand-held instrument has the following advantages. First, it is small and lightweight, making it easy to access tight spaces. Second, surgeons are intimately familiar with hand-held instruments which can leverage the surgeons' experience and skills with little training. Third, a small hand-held instrument offers greater safety because the surgeon can more easily override or remove the instrument in cases of malfunction.

A hand-held instrument, however, poses additional challenges over mechanically-rigid instruments. For example, the drug may need to be accurately delivered to a specific site or layer. Researchers have employed a phase-contrast inverted microscope to guide a capillary injection system and determine the cells injected based on timing. However, challenges remain for accurate injection. First, the surgeon must insert and maintain the tip of the injector at the targeted location with an accuracy that is on the order of tens of micrometers. Second, hand tremor, or physiological motion (e.g. the breathing and/or heartbeat, as well as volitional movement of the surgeon and/or patient) can damage surrounding delicate tissues or cause localized hemorrhage or other injury and pose a high risk to the safety of the patient during injection. The resulting involuntary changes in distance between the injector and surgical tissue surface, although usually on the order of a few hundreds of micrometer at less than 5 Hz, may cause serious error due to the scale of microsurgery. The "injector-tissue" relative motion is especially critical in the case of surface operations such as retina vitreous surgery and cerebral cortex neurosurgery where the fragile tissue's axial involuntary motion is a primary concern that requires high dexterity and constant attention from experienced surgeons.

Currently, no hand held injection system can satisfy all of the above challenges during injection. There remains a need for improved injector systems and methods for microsurgical applications.

SUMMARY

A motion-compensated injector system according to an embodiment includes a handheld tool having a hollow shaft with a distal end for insertion into tissue of a subject. The system also includes an optical coherence tomography-based optical detection system having an optical fiber with a distal end at a fixed distance from the distal end of the hollow shaft, and an optical sensor to receive a signal from the optical fiber. The system further includes an actuator to move the hollow shaft in an axial direction, and a control unit to control the actuator. The optical detection system is configured to monitor a distance between the distal end of the optical fiber and a reference portion of the tissue of the subject, and the control unit controls the actuator to move the hollow shaft to compensate for relative motion between the handheld tool and the portion of the tissue.

According to an embodiment, a method of performing a motion-compensated injection of a material is provided. The method includes providing a handheld injector having a hollow shaft. The hollow shaft has a distal end and is configured to deliver a material. The method also includes providing an optical coherence tomography-based optical detection system having an optical fiber with a distal end at a fixed distance from the distal end of the hollow shaft, and an optical sensor. The method further includes monitoring, with the optical detection system, a distance between the distal end of the optical fiber and a target area for the motion-compensated injection, and controlling a position of the hollow shaft along a longitudinal axis of the hollow shaft to reduce a change in the distance between the distal end of the optical fiber and the target location. The method further includes injecting the material.

BRIEF DESCRIPTION OF THE DRAWINGS

Further objectives and advantages will become apparent from a consideration of the description, drawings, and examples.

DETAILED DESCRIPTION

Figure 1:
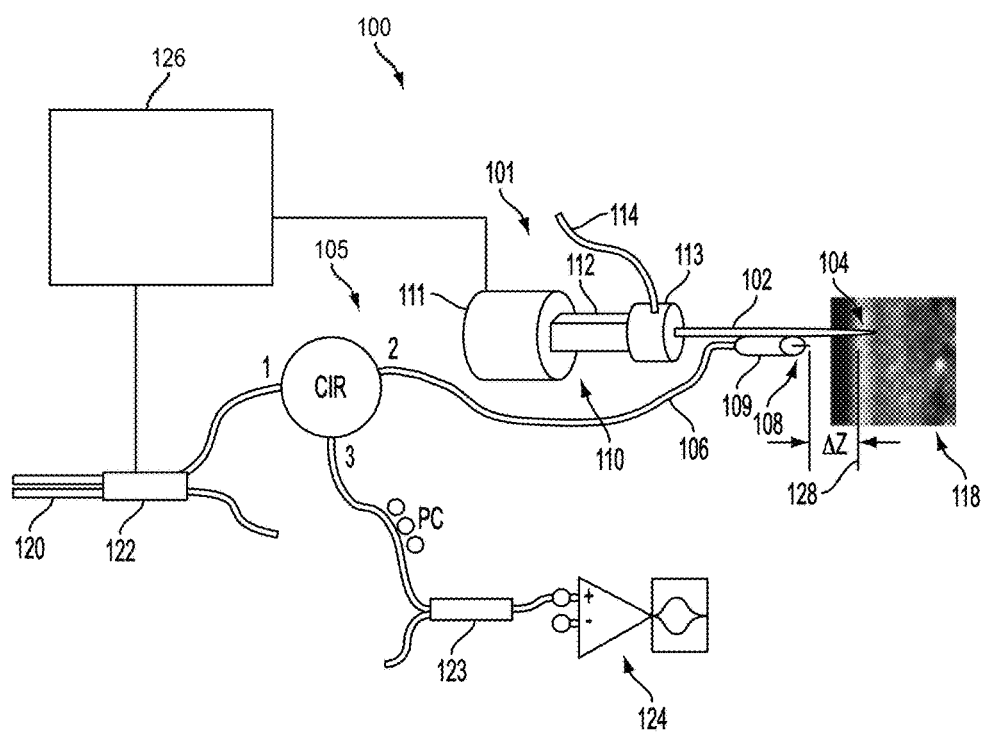
FIG. 1 is a schematic illustration of a motion-compensated injector system according to an embodiment of the current invention.

Some embodiments of the current invention are discussed in detail below. In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated. All references cited in this specification are incorporated herein by reference.

The term "light" as used herein is intended to have a broad meaning that can include both visible and non-visible regions of the electromagnetic spectrum. For example, visible, near infrared, infrared and ultraviolet light are all considered as being within the broad definition of the term "light."

The term "real-time" is intended to mean that the OCT images can be provided to the user during use of the OCT system. In other words, any noticeable time delay between detection and image display to a user is sufficiently short for the particular application at hand. In some cases, the time delay can be so short as to be unnoticeable by a user.

The embodiments of the current invention that are described herein are not intended to be limited to the examples and terminology described. The following applications may contain features and examples that are contemplated as aspects of embodiments of the current invention: U.S. patent application Ser. No. 13/811,077, filed Jan. 18, 2013, which is a U.S. National Stage entry of PCT Application No. PCT/US2011/044693, filed Jul. 20, 2011, which claims priority to U.S. Provisional Application No. 61/365,998, filed Jul. 20, 2010; U.S. patent application Ser. No. 14/114,885, filed Oct. 30, 2013, which is a U.S. National Stage entry of PCT Application No. PCT/US2012/036643, filed May 4, 2012, which claims priority to U.S. Provisional Application No. 61/482,300, filed May 4, 2011; U.S. patent application Ser. No. 13/957,145, filed Aug. 1, 2013, which claims priority to U.S. Provisional Application No. 61/678,397, filed Aug. 1, 2012; and PCT Application No. PCT/US2013/059736, filed Sep. 13, 2013, which is a continuation of U.S. patent application Ser. No. 13/618,810, filed Sep. 14, 2012. These references are hereby incorporated by reference in their entirety.

Some embodiments of the current invention provide a motion-compensated injector system. The injector system may include a handheld tool having a hollow shaft with a distal end for insertion into tissue of a subject. The injector system may also include an optical coherence tomography-based optical detection system having an optical fiber and an optical sensor. The optical fiber may have a distal end at a fixed distance from the distal end of the hollow shaft, and the optical sensor may receive a signal from the optical fiber. The injector system may also include an actuator to move the hollow shaft in an axial direction, and a control unit to control the actuator. The optical detection system can monitor a distance between the distal end of the optical fiber and a reference portion of the tissue of the subject. The reference portion of the tissue may be a tissue surface, or a target location that is within the tissue, or both. The injector system may deliver a material to the target location. The material may include, for example, a fluid, medicine, or implantable device.

Additionally, the control unit may control the actuator to move the hollow shaft to compensate for relative motion between the handheld tool and the portion of the tissue. In some embodiments, the control unit controls the actuator based on a closed-loop proportional-integral-derivative control algorithm. The control unit and the actuator may reduce or eliminate a change in the distance between the distal end of the optical fiber and the reference portion of the tissue that would result from one or both of a motion of the reference portion and a motion of a hand of an operator of the handheld tool. The motion of the reference portion and the motion of the operator's hand may be voluntary or involuntary motion. The motion of the operator's hand may be, for example, a hand tremor of the operator. At the start of and during injection, the positioning of the injector may be even harder to maintain for an operator without motion compensation. Accordingly, the control unit and the actuator may reduce or eliminate the change in the distance during an injection performed by the injector system, including the initiation of the injection of the material and while the material is being injected. In some embodiments, the sensor can monitor the position of the reference portion in real time.

Some of the embodiments of the current invention use a single fiber probe as a CP-OCT distance sensor and a high-speed piezo-electric micro linear motor for one-dimensional actuation. The distance between the distal end of the injector's hollow shaft and the target for injection may be determined from the OCT signal by, for example, an automatic edge-searching algorithm. The micro linear motor may be controlled by a computer, for example, according to feedback from the CP-OCT distance sensor.

Though a desired depth or position of injection may be known, the tissue into which the injection is being made may include a variety of tissue layers and the tissue may be deformable. For example, the tissue may deform by a thickness of one or more layers changing when the hollow shaft of the injector is inserted into the material. The tissue may also deform by movement of the subject or the specific tissue itself. Accordingly, the optical detection system may detect deformation of the tissue resulting from at least one of movement of the tissue and insertion of the hollow shaft into the tissue, and the control unit can control the actuator to compensate for the deformation of the tissue.

In some embodiments, the injector system may include a reservoir in fluid communication with the hollow shaft. The reservoir may move fluid, via an applied pressure, through the hollow shaft and to the target location, for example. The reservoir can be, for example, a syringe. The reservoir may apply pressure via either manual or electronic means.

In some embodiments, the optical detection system uses common-path optical coherence tomography. The optical fiber may include a bare single-mode fiber with a protective sheath. At least a portion of the single-mode fiber with the protective sheath may be parallel to the hollow shaft of the injector system. In some embodiments, the hollow shaft and/or the optical fiber may be detachable from a remainder of the motion-compensated injector system. Accordingly, the hollow shaft and the optical fiber are disposable. The type of optical coherence tomography (OCT) on which the optical detection system is based may be, for example, one of swept source or time encoded frequency domain OCT, spatial domain or Fourier transform OCT, and frequency domain OCT. The optical detection system may perform an imaging of the tissue via optical coherence tomography during one or more of before, during, and after performance of the injection into the tissue. The imaging during and after the injection may include determining a depth or location of the injected material.

In some embodiments, the injector system may also include a measuring unit to measure an amount of material injected by the injector system. Accordingly, the control unit can control the actuator to withdraw the hollow shaft from the tissue when the amount of material injected, as measured by the measuring unit, reaches a predetermined or desired amount. In some embodiments, the injector system further includes a signaling unit to signal the operator of the injector system when the amount of material injected, as measured by the measuring unit, reaches the predetermined or desired amount.

The actuator of the injector system according to some embodiments may include a lead zirconium titanate (PZT) motor and a rod to which the hollow shaft is directly or indirectly fixed. The PZT motor can thus drive the rod to move the hollow shaft. The injector system may include a user-operable mechanism for selectively turning on and off at least one of the actuator and the optical detection system. "Turning on and off" may include, for example, controlling when the actuator is able to change the position of the hollow shaft.

Some embodiments of the current invention can be integrated into standard freehand injectors and can enable surgeons to make precise injections safely and effectively.

Some embodiments of the current invention provide a method of performing a motion-compensated injection of a material. The method may include providing a handheld injector comprising a hollow shaft, the hollow shaft having a distal end and being able to deliver a material. The method also includes providing an optical coherence tomography-based optical detection system having an optical fiber with a distal end at a fixed distance from the distal end of the hollow shaft, and having an optical sensor. The method may further include monitoring, with the optical detection system, a distance between the distal end of the optical fiber and a target area for the motion-compensated injection. The method may also include controlling a position of the hollow shaft along a longitudinal axis of the hollow shaft to reduce a change in the distance between the distal end of the optical fiber and the target location. The method may also include injecting the material.

According to some embodiments, the method may include monitoring the amount of the material injected at the target location. The method may also include controlling the actuator to at least partially withdraw the hollow shaft when a predetermined or desired amount of the material is injected.

In some embodiments, the distal end of hollow shaft may be brought into the proximity of a target area for injection by, for example, an operator of the injector. After being brought into proximity of the target area, axial motion of the hollow shaft may be at least partially automated. For example, in addition to being moveable by the hand of the operator, an actuator may be controlled to bring the distal end of the hollow shaft to the target location, and motion-compensation may be performed to control a distance between the target location (or some other portion of the subject of injection) and the distal end of the optical fiber. A user performing the method may be able to selectively turn on and off the motion-compensation.

The controlling of the position of the hollow shaft may be performed during at least one of before, during, and after the injection of the material. In some embodiments, the method may include imaging the target area using the optical detection system during at least one of before, during, and after injecting the material. The method may also include determining a position of the material after injecting the material. In some embodiments, the optical detection system uses common-path optical coherence tomography.

The systems and methods of injection described above may apply to injections into biological material, such as human tissue, but the systems and methods are not limited thereto. For example, the injection may be for any object or system for which motion-compensated injection can be useful.

FIG. 1 shows a schematic illustration of a motion-compensated injector system 100 according to an embodiment of the current invention. The injector system 100 includes a handheld tool 101 that includes a hollow shaft 102. A distal end 104 of the hollow shaft 102 is configured for insertion into a person or object for delivering a material to be injected. FIG. 1 shows a section of tissue 118 in which the distal end 104 of the hollow shaft 102 is inserted. An optical detection system 105 includes an optical fiber 106 that is attached to the hollow shaft 102 such that a distal end 106 of the optical fiber 106 is a fixed distance from the distal end 104 of the hollow shaft 102. The optical detection system 105 is configured to output a signal for the determination of a distance between the distal end 104 of the hollow shaft 102 and the targeted portion for injection. A sheath 109 surrounds at least a portion of the optical fiber 106. Though the optical fiber 106 is attached to the hollow shaft 102 in FIG. 1, embodiments of the invention are not limited to such a configuration. For example, the optical fiber 106 may be mounted onto some other portion of the handheld tool 101 or arranged in some other manner so as to be a fixed distance from the distal end 104 of the hollow shaft 102.

An actuator 110 includes a motor 111, such as a lead zirconium titanate (PZT) motor, that is attached to a rod 112 which is attached or coupled to the hollow shaft 102. The motor 111 moves the rod 112 to change the position of the hollow shaft 102 along an axial direction of the hollow shaft 102. As shown in FIG. 1, a T-shaped connector 113 can be used to connect the rod 112 to the hollow shaft 102, and a hose 114 to the hollow shaft 102. The hose 114 can be used to deliver the material to be injected.

A control unit 126 may be in communication with the handheld tool 101 and the optical detection system 105. As discussed above and in more detail further below, the control unit 126 can control the actuator 110 to control or adjust the distance between the distal end 108 of the optical fiber 106 and a portion of the tissue or object into which the injection is being made. The distance between the distal end 108 of the CP-SSOCT fiber sensor and the tissue interface 128 is represented by Δz. Accordingly, the distance between the distal end 104 of the hollow shaft 102 and the targeted portion for injection can be indirectly controlled because the distance between the distal end 104 of the hollow shaft 102 and the distal end 108 of the optical fiber 106 is known.

The control unit 126 may include, for example, a data processor, software, or a combination of hardware and software. The control unit 126 can be a dedicated "hard-wired" device, or it can be a programmable device. For example, it can be, but is not limited to, a personal computer, a work station or any other suitable electronic device for the particular application. In some embodiments, it may be integrated into a unit or it could be attachable, remote, and/or distributed.

In some embodiments, the control unit 126 is further configured to determine an amount, speed and/or direction of movement of the hollow shaft 102 to be moved by the actuator 110 to counter motions of the distal end 104 of the hollow shaft 102 relative to the target portion or tissue 118 during use or injection.

In some embodiments, the optical detection system 105 can have a light source comprising a superluminescent light emitting diode. In some embodiments, a spectrometer can be used as an optical detector of the optical detection system 105. In other embodiments, the light source can be a wavelength swept laser and the optical detector can be a photodetector. The broad concepts of the current invention are not limited to these particular examples.

As shown in the embodiment in FIG. 1, a laser 120 may be used as a light source for the OCT optical detection system 105. For example, the laser 120 may be optically coupled to the optical fiber 106. In some embodiments, the light passes through a coupler 122, through a circulator CIR to the distal end 108 of the optical fiber 106. An OCT signal is sent back through the optical fiber 106 from the tissue 118, and circulated through the circulator CIR to the unbalanced detector 124, passing a polarized controller PC and a coupler 123. For example, the couplers 122, 123 can be 2×2 couplers, as shown in FIG. 1. The optical fiber 106 may provide a common transmit and receive optical path such that the optical detection system is a common-path optical coherence tomography system (CP-OCT).

Figure 2:
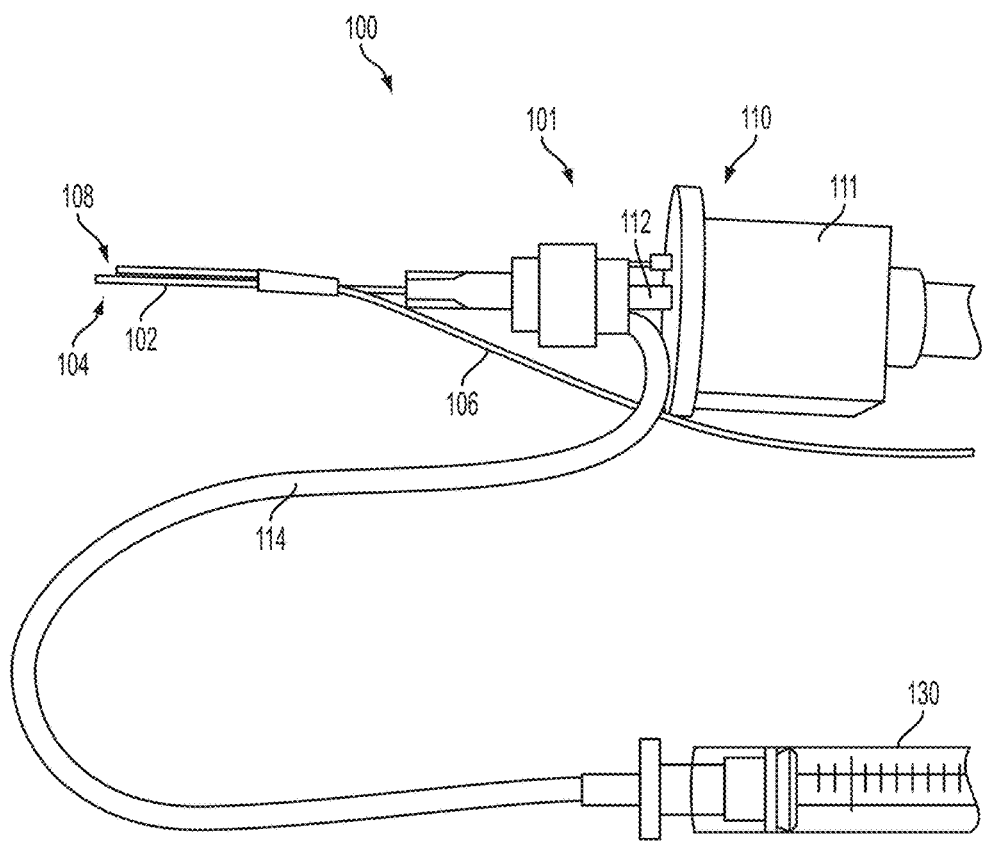
FIG. 2 shows a motion-compensated injector system according to an embodiment of the current invention.

FIG. 2 shows an example of an injector system 100 according to an embodiment of the current invention. Portions of the injector system 100 previously described will not be repeated here. In FIG. 2, the hose 114 is connected at one end to the hollow shaft 102 and at another end to a syringe 130. The syringe 130 may be used to supply the material to be injected to the hollow shaft 102. A 25-gauge hypodermic needle is used as the hollow shaft 102 in FIG. 2, and the optical fiber 106 is used to form part of a common path-optical coherence tomography (CP-OCT) system. The motor 111 is a PZT motor, but other types of motors or actuators may be used.

Figure 3:
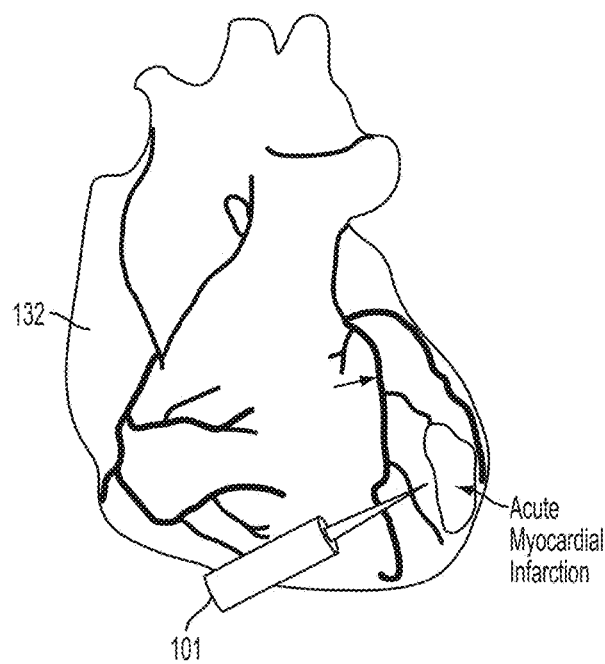
FIG. 3 is an illustration of one example of an application of a motion-compensated injector system according to an embodiment of the current invention.

One application of the injector system according to an embodiment of the current invention is shown in FIG. 3. A handheld tool 101 of a motion-controlled injector system can be used, for example, to deliver therapeutic materials to the area of a heart 132 that has suffered an acute myocardial infarction. A person of ordinary skill in the art would understand that this is but one example of many potential applications for embodiments of the current invention.

The following provides some examples according to some embodiments of the current invention. The general concepts of the current invention are not limited to these particular examples that are provided to explain concepts of the current invention.

EXAMPLES

The following example pertains to a novel intelligent injection system using common-path swept source optical coherence tomography (CP-SSOCT) as a ranging sensor to detect the distance between the tissue and the tip of the CP-SSOCT fiber sensor attached to a 25-gauge hypodermic needle. Smaller or larger needles and delivery devices are also proposed. As shown in the example of FIG. 2, the kernel part of the injector includes the aforementioned CP-SSOCT sensor, 25-gauge hypodermic needle, a syringe, a "hose" or other conduit for the fluid, lead zirconium titanate (PZT) motor with a rod to drive the needle and a mechanical T-shape connector to integrate hose, rod and needle. A 1310 nm swept source laser with a wide tuning range of 100 nm (Axsun Technologies, Inc.) was used as the OCT engine, operating at a 50 kHz repetition rate with an axial resolution of 19 μm. In this example, a bare single-mode fiber (SMF) with a protective sheath oriented parallel to a 25-gauge hypodermic needle (though smaller needles may also be used) was customized as a common-path OCT sensor to detect the distance between the tissue and fiber sensor tip. This distance is maintained by a real-time feedback PZT motor with a resolution of ~5 μm (or less than 5 μm), which also dramatically reduces hand tremor, and potential for accidental needle-associated injuries caused by the surgeon using a closed-loop PID active control algorithm.

To maximize the sensitivity of the CP-OCT sensor, the fiber surface was polished to have a reference power optimized to approximately 21 μW with a sensitivity of up to 70 dB. The dynamic range of a general OCT system in biological tissue such as retina is less than 50 dB. The performance of the CP-SSOCT is good enough to function as a senor to detect the interface of biological tissue and air instead of being used as an imaging probe. The power incident on the sample is around 10 mw. The OCT signal is circulated back to an unbalanced detector (PDB 410, Thorlabs, Newton, N.J., USA) via a circulator (see the schematic shown in FIG. 1). Only the positive input port of the dual-balanced detector was used to collect signal in the CP-SSOCT.

In preliminary studies, a hypodermic needle with the CP-OCT fiber sensor attached away from the needle tip at a distance of around 1.8 mm was inserted into the test tissue. The distance between the tissue and fiber sensor was measured by an A-scan OCT signal that was collected by a 12-bit PCI Express Digitizer (ATS 9350, Alazartech, Canada). The OCT signal was obtained after DC removal and Fourier transform using a graphics-processing unit (GPU). Because the highest hand tremor frequency is less than 50 Hz, the sampled 50 KHz OCT signal was down-sampled to 100 Hz for data processing and storage. To detect the interface between tissue and air, an effective peak detection algorithm is critical to determining the peak position of the OCT A-line signal coming from the interface. The interferometric CP-SSOCT sensor signal at position $\Delta z$ after Fourier transform can be described as follows:

$$I(2n\Delta z)=(\rho/2e)Sqrt(PrPs)Rs\ L(2n\Delta z)\exp(i2k0n\delta z) \quad (1)$$

where n is the tissue refractive index, $\rho$ is the detector responsivity, and e is the electronic charge. Pr and Ps are the reference and sample power, respectively. Rs is the sample reflection coefficient; $L(2n\Delta z)$ is the normalized-amplitude mutual coherence function; the last term is phase related to central wave number k0, n and fractional imaging depth. The above equation shows that the OCT signal has a peak value at the air-tissue interface since Rs is at a maximum at this location. Simple maximum value peak detection works very well for dry phantoms or less scattering biological tissue. However, it introduces high root mean square error (RMSE) of 30~50 μm for wet or otherwise strong scattering biological tissue. To reduce the false alarm rate of peak detection caused by the random speckle noise in turbid media, the mass center of local peaks was calculated to suppress the impact of strong speckle signals scattering back from the deeper layers of the tissue. Here it was assumed that peak OCT signal is the interface between the tissue and air. This mass center algorithm significantly improves the performance for accurate peak detection with a root mean square (RMS) of 2~3 μm for still strongly scattering biological tissue with a performance enhancement at least 10 times that of the simple peak maximum value detection algorithm. The customized injection depth is 450 μm, which is indirectly maintained by a PZT motor to control the distance between the CP-SSOCT fiber sensor and the tissue interface, $\Delta z$, illustrated in FIG. 1.

Figure 4:
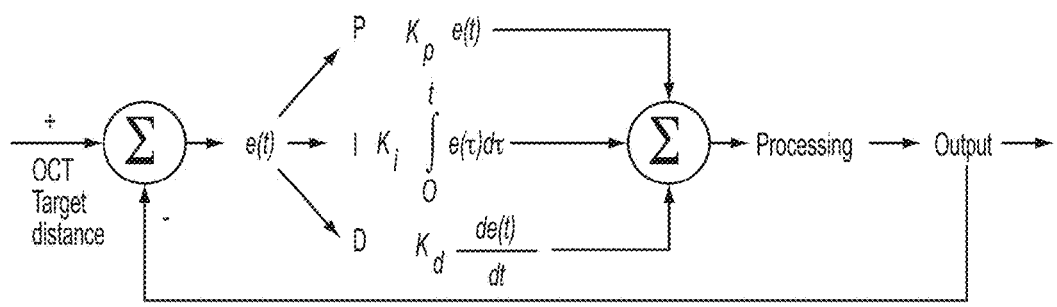
FIG. 4 shows an example of a control process of a motion-compensated injector system according to an embodiment of the current invention.

In reality, the desired injection depth can vary with the location of the CP-SSOCT fiber sensor and target depth setting. The maximum injection depth can be up to 4.5 mm limited by the OCT coherence length; the minimum injection depth is on the order of the axial resolution, 19 μm, of the OCT system. To improve the accuracy of PZT compensation, a zero-padding sub-pixel technique was used to improve the axial resolution. The PID control algorithm was employed to adaptively move the rod of the PZT motor that is connected to the hypodermic needle. The difference between the target position and the detected OCT peak is called error, e(t). The PZT motor controls the motion of hypodermic needle to compensate the error so as to consistently maintain the desired penetration depth. The control output of the PZT motor can be described by the following equation:

$$u(t)=K_p e(t)+K_i\int_0^t e(s)ds+K_d de(t)/dt \quad (2)$$

where $K_p$, $K_i$ and $K_d$ are the proportional gain, integral gain and derivative gain, respectively. The above parameters are adjusted based on experience and RSME. These parameters are different from the values obtained for active tracking in air space since the tissue damping effects have an impact on the performance of the PID controller. A block diagram of PID control for distance maintaining is illustrated in FIG. 4. The output is converted into the control voltage and compensation frequency of the PZT motor.

Figure 5:
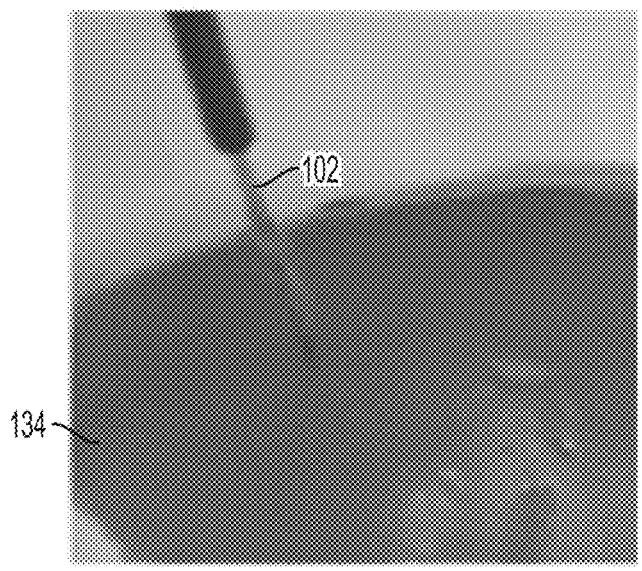
FIG. 5 shows an injector inserted into an object for an example according to an embodiment of the current invention.
Figure 6:
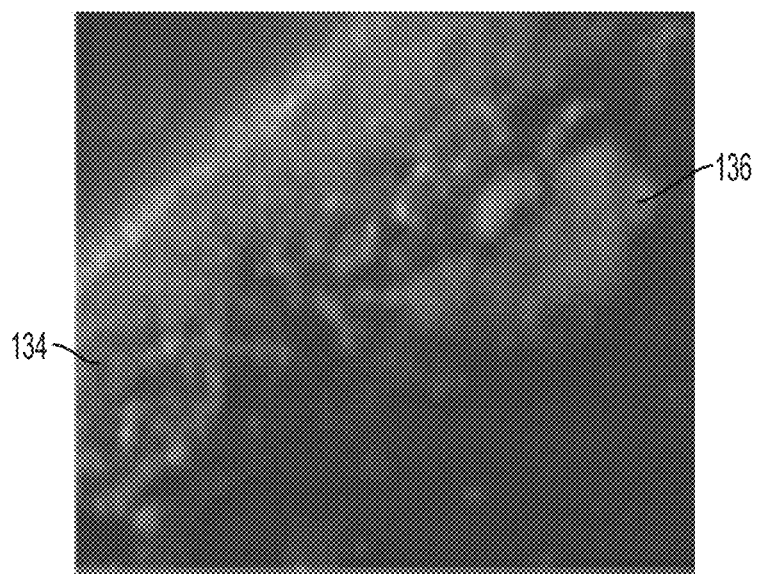
FIG. 6 shows a cross-section of the object in FIG. 5 after an injection for an example according to an embodiment of the current invention.
Figure 7:
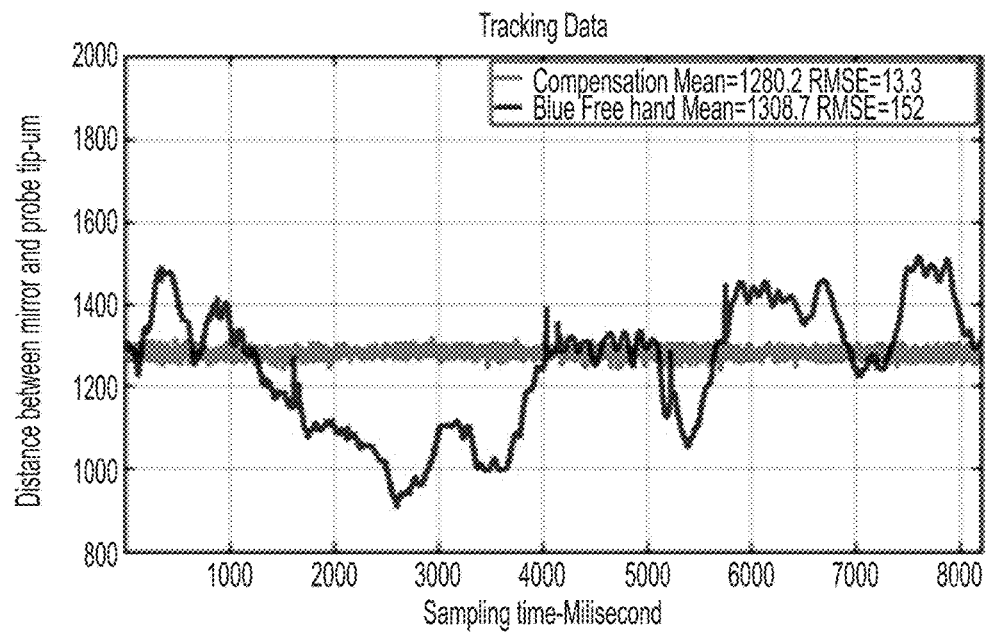
FIG. 7 shows a non-motion-compensated result and a motion-compensated result of the distance between an optical coherence tomography sensor-based detection system and injection surface for an example according to an embodiment of the current invention.
Figure 8:
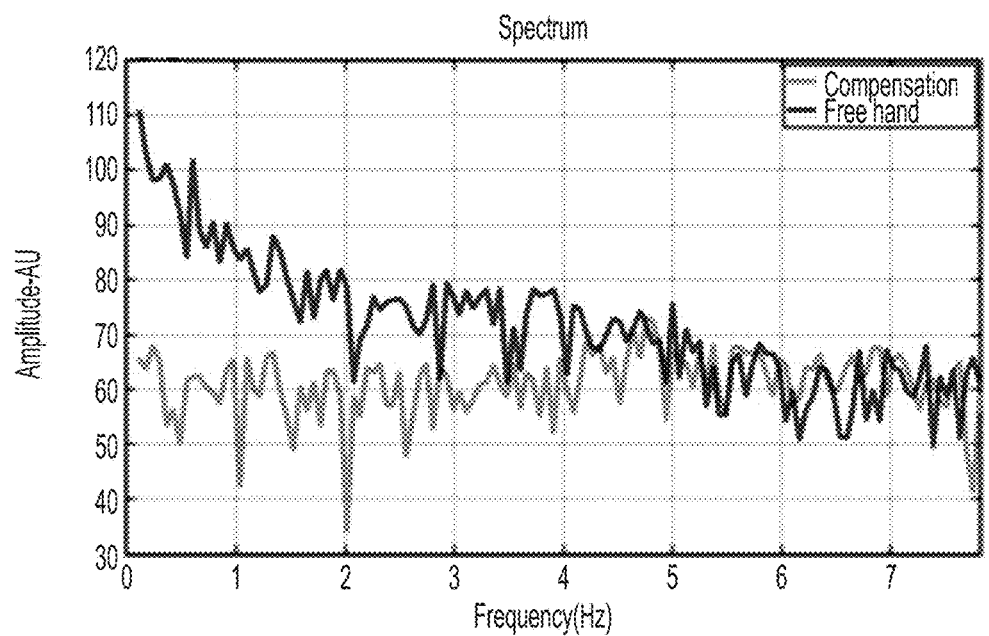
FIG. 8 shows a non-motion-compensated result and a motion-compensated result for an example according to an embodiment of the current invention.

The injector was first tested in a wet phantom model illustrated in FIG. 5. Specifically, FIG. 5 shows a piece of tomato, which is soft and has low damping effects for the needle to easily be inserted into. The 25-gauge hypodermic needle was first inserted into the tissue in a very shallow layer, and then the PZT motor was turned on to drive the needle to the desired injection depth. After that, the protein solution (milk) was delivered into the target site at a depth of 450 μm via a hose and a syringe with manual pumping. The PZT motor actively maintained the injection depth during the injection. After injection, the injected milk was imaged by 850 nm spectrum domain OCT (SDOCT) at an axial resolution of around 3 μm with a scanning range of 1 mm by 1 mm. A volume of milk was clearly visible on the right side in FIG. 6. The injection depth was around 450 μm based on the evaluation using 850 nm SDOCT. The trace in green in FIG. 7 shows the active compensation distance during the injection with RMSE of 13.3 μm, which significantly reduces the hand tremor and constantly maintains an offset distance of 1280 μm from the tissue surface to the fiber sensor-polishing surface called the reference arm of the CP-SSOCT. The trace in blue was not compensated by the PZT motor with RMS of 152 μm and mean value of 1308 μm. This shows a strong injection depth fluctuation during injection if the PZT compensation is off. The spectrum in FIG. 8 in green shows that hand tremor frequencies lower than 5 Hz were significantly suppressed by the intelligent injector. The spectrum of free hand injection is shown in blue with a large amplitude around the low frequency region less than 5 Hz since the active PZT motor is off.

Figure 9:
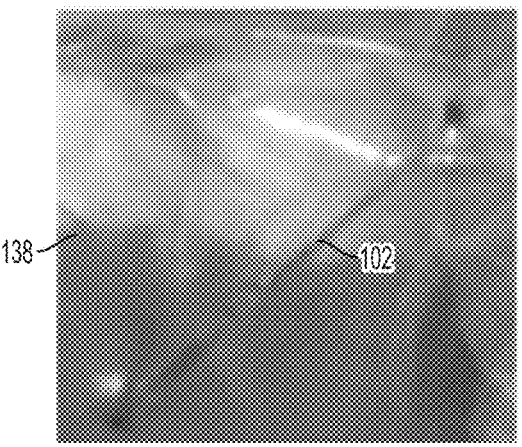
FIG. 9 shows an injection into tissue for an example according to an embodiment of the current invention.
Figure 10:
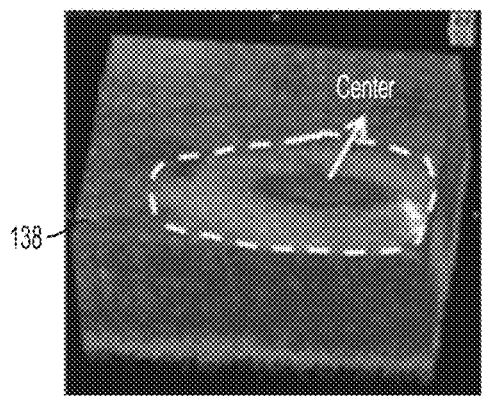
FIG. 10 shows an optical coherence tomography visualization of the material injected into the tissue shown in FIG. 9 for an example according to an embodiment of the current invention.
Figure 11:
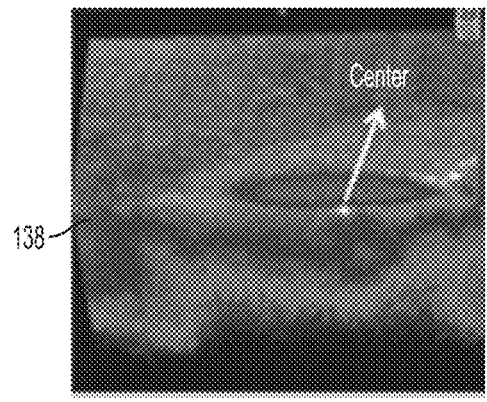
FIG. 11 shows a cross-sectional view of the visualization shown in FIG. 10 for an example according to an embodiment of the current invention.
Figure 12:
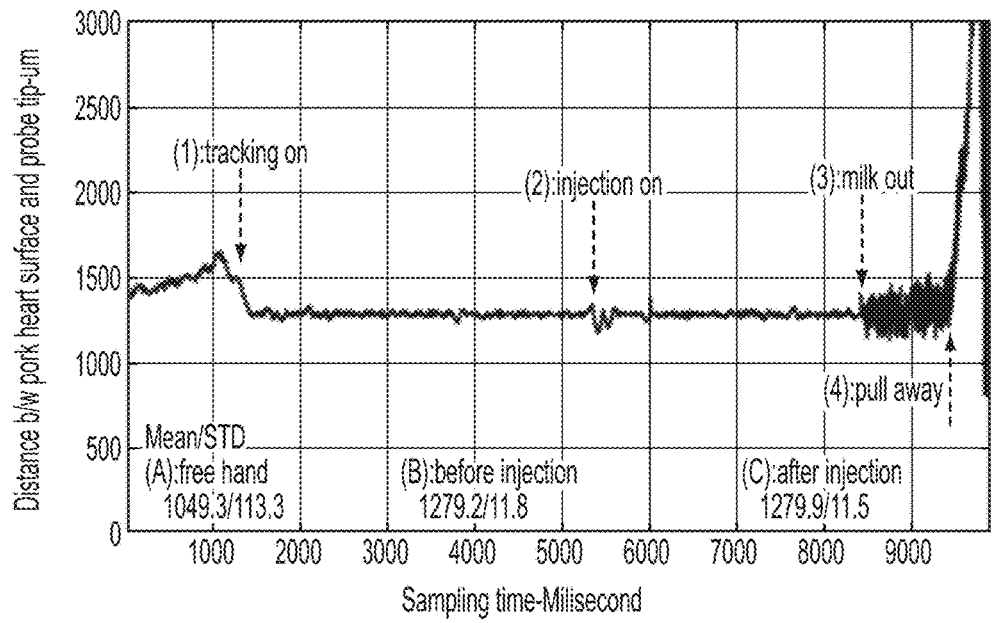
FIG. 12 shows a result of the distance between the tissue surface and optical coherence tomography sensor-based detection system for the injection shown in FIG. 9 for an example according to an embodiment of the current invention.
Figure 13:
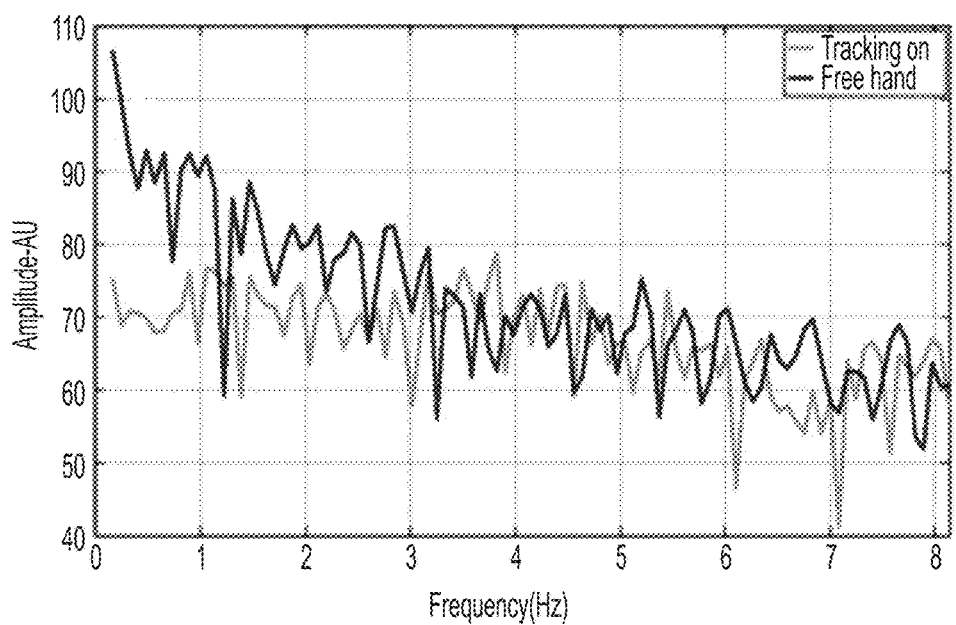
FIG. 13 shows a spectrum of the result shown in FIG. 12 for an example according to an embodiment of the current invention.

A wet biological tissue—specifically, swine heart—was used to further test the performance of the proposed injector. FIG. 9 shows a sample of the swine heart 138 used in this example. Wet tissues are more difficult than dry tissues to test the injector since wetting of the sensor significantly diminishes the sensitivity of the OCT sensor. FIG. 9 demonstrates milk injection into the swine heart 138 that has a much stronger damping effect than tomato. FIG. 10 is the 3-D visualization after injection and after removing the top 100 μm. FIG. 11 is the 3-D visualization of the injection volume cut from the injection center. FIG. 12 shows the trace of the distance between the heart surface and CP-OCT sensor. The desired distance was 1280 μm. The mean and RMS for free hand was 1049.3±113.3 μm. The PZT motor was actively turned on at position (1) in FIG. 12, which indicates much less tremor with mean and RMSE of 1279.2±11.8 μm. The milk was then injected into the tissue starting at position (2). A disturbance of the trace in the order of 40 μm can be found at this position due to the sudden initiation of injection. The mean and RMS is 1279.9±11.5 μm during injection, which reflects a stable and smooth injection process due to the PID intelligent tremor compensation. The milk leaked out of the heart tissue after around 3-seconds of continuous injection at position (3). The trace stability was apparently diminished by the capillary effects that then wet the sensor. The needle was pulled out of the heart at position (4). FIG. 13 is the spectrum analysis of the hand tremor. Lower tremor frequencies (less than 3.5 Hz)

were clearly compensated by the PZT motor with a RMS less than 12 µm, which is much less than that of free hand, on the order of 113 µm. Since cardiac muscle has much stronger damping effects than tomato tissue, hand tremor was partially reduced by the cardiac muscle itself. That is why hand tremor frequencies ranging from 3.5 Hz to 5 Hz are present in the tomato model but absent in swine heart model in FIG. 13. FIG. 10 shows a 3-D visualization of the milk inside of the tissue with a 0.6*0.7*0.5 mm section captured by an 850 nm SDOCT system. The residual milk at the needle center can be clearly observed in FIG. 10. The milk that diffused to the surrounding region was highlighted by the circle in white. FIG. 11 is the cross-section view of FIG. 10 along the injection center.

The performance of the injection system depends heavily on the sensitivity of the CP-SSOCT sensor, peak detection algorithm, and PID gain parameters. The peak detection algorithm is very sensitive to the sensor design and the diameter of the protection sheath. With a small diameter sheath the injector can be made very compact, but this does decrease the numerical aperture of the CP-SSOCT probe for collection of the back scattering OCT signal. In addition, in the current design the narrow diameter of the sheath may generate capillary action that wets the sensor and diminishes the sensitivity of the OCT sensor. The injecting time during which the intelligent injector is maintained inside the tissue determines the volume injected. The precise control of the inside depth improves the reliability and repeatability of injection. The tracking on the injector has good mechanical stability. This can be confirmed by the RMS of 12 µm while the tracking is turned on. Conversely the RMSE of free hand injection is much greater at 113 µm. The performance improves around 9.4 times in active tracking mode. Hence, the operation and handling of the injection system facilitates the procedure, reduces the training time and the amount of skill required for high precision injections. The results also show that there is a disturbance in the trace at 40 µm in FIG. 12 due to the sudden initiation of injection in the swine heart; however, the trace is much smoother in the softer tissue of the tomato resulting in no disturbance. This may be attributed to the fact that heart muscle tissue is much denser and more tightly interconnected than that of tomato, so it is difficult to immediately inject the milk into the tissue manually. In an analogous result, the damping effect is also much stronger in muscle tissue than in tomato. Here, evidence is shown that hand tremor of up to 5 Hz is compensated in the soft tissue case. However, it is only compensated at up to 3.5 Hz in the more dense swine heart. It is believed that the frequency from 3.5 Hz to 5 Hz was naturally compensated by the inherent damping effects of the denser muscle.

To conclude, demonstrated for the first time was a CP-SSOCT-based intelligent high precision injector that could theoretically inject drugs at a specific site with a resolution on the order of 10 µm. The drug injection depth is maintained by an active PZT motor, which could also significantly reduce hand tremor of the surgeon using a closed-loop PID control algorithm based on GPU computing. Swine heart was employed to test the performance of the injector in biological tissue. Potential applications of this novel technology might include, but not be limited to, delicate tissues such as retina or robust tissues such as muscle/heart by adjusting the diameter of the needle and target injection depth to avoid localized hemorrhage and tissue destruction at the injection site.

REFERENCES

1. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science 254, 4 (1991).

2. A. F. Fercher, C. K. Hitzenberger, G. Kamp, and S. Y. El-Zaiat, "Measurement of intraocular distances by backscattering spectral interferometry," Opt. Commun. 17, 6 (1995).

3. R. Leitgeb, C. K. Hitzenberger, and A. F. Fercher, "Performance of fourier domain vs. time domain optical coherence tomography," Opt. Express 11, 6 (2003).

4. J. F. d. Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 3 (2003).

5. M. A. Choma, M. V. Sarunic, C. Yang, and J. A. Izatt, "Sensitivity advantage of swept source and Fourier domain optical coherence tomography," Opt. Express 11, 7 (2003).

6. M. Yamanari, S. Makita, V. D. Madjarova, T. Yatagai, and Y. Yasuno, "Fiber-based polarization-sensitive Fourier domain optical coherence tomography using B-scan-oriented polarization modulation method," Opt. Express 14, 6502 (2006).

7. M. Zhao and J. A. Izatt, "Single camera sequential scan based polarization sensitive SDOCT for retinal imaging," Opt. Lett. 34, 3 (2009).

8. M. Zhao, Y. Huang, and J. U. Kang, "Sapphire ball lens-based fiber probe for common-path optical coherence tomography and its applications in corneal and retinal imaging," Opt. Lett. 37, 3 (2012).

9. S. H. Yun, G. J. Tearney, J. F. d. Boer, N. Iftimia, and B. E. Bouma, "High-speed optical frequency-domain imaging," Opt. Express 11, 11 (2003).

10. L. An and R. K. Wang, "In vivo volumetric imaging of vascular perfusion within human retina and choroids with optical micro-angiography," Opt. Express 16, 15 (2008).

11. W. A. Benalcazar, W. Jung, and S. A. Boppart, "Aberration characterization for the optimal design of high-resolution endoscopic optical coherence tomography catheters," Opt. Lett. 37, 3 (2012).

12. Y. Zhu, N. G. Terry, J. T. Woosley, N. J. Shaheen, and A. Wax, "Design and validation of an angle-resolved low-coherence interferometry fiber probe for in vivo clinical measurements of depth-resolved nuclear morphology," J. Biomed. Opt. 16 (2011).

13. Y. Mao, S. Chang, S. Sherif, and C. Flueraru, "Graded-index fiber lens proposed for ultrasmall probes used in biomedical imaging," Appl. Opt 46, 8 (2008).

14. J. U. Kang, J. -H. Han, X. Liu, K. Zhang, C. G. Song, and P. Gehlbach, "Endoscopic Functional Fourier Domain Common-Path Optical Coherence Tomography for Microsurgery," IEEE J. Sel. Top. Quant. Electron. 16, 12 (2010).

15. G. J. Tearney, M. E. Brezinski, B. E. Bouma, S. A. Boppart, C. Pitris, J. F. Southern, and J. G. Fujimoto, "In vivo endoscopic optical biopsy with optical coherence tomography," Science 276, 3 (1997).

16. S. Liang, A. Saidi, J. Jing, G. Liu, J. Li, J. Zhang, C. Sun, J. Narula, and Z. Chen, "Intravascular atherosclerotic imaging with combined fluorescence and optical coherence tomography probe based on a double-clad fiber combiner," J. Biomed. Opt. 17, 3 (2012).

17. X. Li, T. H. Ko, and J. G. Fujimoto, "Intraluminal fiber-optic Doppler imaging catheter for structural and functional optical coherence tomography," Opt. Lett. 26, 3 (2001).

18. V. X. D. Yang, Y. X. Mao, N. Munce, B. Standish, W. Kucharczyk, N. E. Marcon, B. C. Wilson, and I. A. Vitkin, "Interstitial Doppler optical coherence tomography," Opt. Lett. 30, 3 (2005).

19. K. Zhang and J. U. Kang, "Common-path low-coherence interferometry fiber-optic sensor guided microincision " J. Biomed. Opt. 16, 5 (2011).

20. R. Pepperkok, C. Schneider, L. Philipson, and W. Ansorge, "Single cell assay with an automated capillary injection system," Exp. Cell. Res. 17, 8 (1988).

21. S. Mitragotri, "Current status and future prospects of needle-free liquid jet injectors," Nature Rev. Drug Discov. 5, 6 (2006).

22. T. Peters and K. Cleary, *Image-Guided Interventions: Technology and Applications*, Springer, 2008.

23. Zhang, K., Wang, W., Han, J -H., Kang, J. U., "A surface topology and motion compensation system for microsurgery guidance and intervention based on common-path optical coherence tomography," IEEE Trans. Biomed. Eng., 56(9), 2318-2321 (2009).

24. Zhang, K., Akpek, E. K., Weiblinger, R. P., Kim, D -H., Kang, J. U., and Ilev, I. K., "Noninvaseive volumetric quality evaluation of post-surgical clear corneal incision via high-resolution Fourier-domain optical coherence tomography," Electron. Lett., 46(22), 1482-1483 (2010).

25. Zhang, K. and Kang, J. U., "Real-time 4D signal processing and visualization using graphics processing unit on a regular nonlinear-k Fourier-domain OCT system." Opt. Express, 18(11), 11772-11784 (2010).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore understood that, within the scope of the claims and their equivalents, the invention may be practiced otherwise than as specifically described.

We claim:

1. A motion-compensated injector system comprising:
    a handheld tool comprising a hollow shaft with a distal end configured for insertion into tissue of a subject to deliver a material to a target location of the tissue of the subject through the hollow shaft;
    an optical coherence tomography-based optical detection system comprising:
        an optical fiber having a distal end at a fixed distance from the distal end of the hollow shaft, and
        an optical sensor configured to receive a signal from the optical fiber;
    an actuator integrated into the handheld tool, the actuator configured to move the hollow shaft in an axial direction, the actuator comprising a linear motor directly connected to a rod to which the hollow shaft is fixed, the linear motor driving the rod to move the hollow shaft; and
    a control unit to control the actuator,
    wherein the optical detection system is configured to monitor a distance between the distal end of the optical fiber and a reference portion of the tissue of the subject,
    wherein the control unit controls the actuator to move the hollow shaft to compensate for relative motion between the handheld tool and the portion of the tissue,
    wherein the control unit is configured to control the actuator based on a closed-loop proportional-integral-derivative control algorithm to compensate for deformation of the tissue during insertion of the hollow shaft, and
    wherein the optical fiber is adjacent but not concentric to the hollow shaft.

2. The motion-compensated injector system of claim 1, wherein the reference portion of the tissue is at least one of a tissue surface and the target location, wherein the target location is within the tissue.

3. The motion-compensated injector system of claim 1, wherein the control unit and the actuator are configured to at least reduce a change in the distance between the distal end of the optical fiber and the reference portion of the tissue resulting from at least one of a motion of the reference portion and a motion of a hand of an operator of the handheld tool.

4. The motion-compensated injector system according to claim 3, wherein the motion of the hand is a hand tremor of the operator.

5. The motion-compensated injector system according to claim 3, wherein the control unit and the actuator are configured to at least reduce the change in the distance during an injection performed by the injector system.

6. The motion-compensated injector system of claim 1, wherein the sensor is configured to monitor the position of the reference portion in real time.

7. The motion-compensated injector system of claim 1:
    wherein the optical detection system is configured to detect deformation of the tissue resulting from at least one of movement of the tissue and insertion of the hollow shaft into the tissue, and
    wherein the control unit is configured to control the actuator to compensate for the deformation of the tissue.

8. The motion-compensated injector system of claim 1, further comprising:
    a reservoir in fluid communication with the hollow shaft, the reservoir being configured to move fluid, via an applied pressure, through the hollow shaft.

9. The motion-compensated injector system of claim 8, wherein the reservoir is a syringe.

10. The motion-compensated injector system of claim 1, wherein the optical detection system uses common-path optical coherence tomography.

11. The motion-compensated injector system of claim 1, wherein the optical fiber comprises a bare single-mode fiber with a protective sheath, the single-mode fiber with the protective sheath being parallel to the hollow shaft.

12. The motion-compensated injector system of claim 1, wherein the hollow shaft and the optical fiber are detachable from a remainder of the motion-compensated injector system.

13. The motion-compensated injector system of claim 12, wherein the hollow shaft and the optical fiber are disposable.

14. The motion-compensated injector system of claim 1, wherein a type of optical coherence tomography (OCT) on which the optical detection system is based is one of swept source or time encoded frequency domain OCT, spatial domain or Fourier transform OCT, and frequency domain OCT.

15. The motion-compensated injector system of claim 1, further comprising:
    a measuring unit configured to measure an amount of material injected by the injector system.

16. The motion-compensated injector system of claim 15, wherein the control unit controls the actuator to withdraw the hollow shaft from the tissue when the amount of material injected, as measured by the measuring unit, reaches a predetermined amount.

17. The motion-compensated injector system of claim 15, further comprising:
a signaling unit configured to signal an operator of the injector system when the amount of material injected, as measured by the measuring unit, reaches a predetermined amount.

18. The motion-compensated injector system of claim 1, wherein the optical detection system is configured to perform an imaging of the tissue via optical coherence tomography after an injection into the tissue is performed by the injector system.

19. The motion-compensated injector system of claim 1, wherein the linear motor is a lead zirconium titanate motor.

20. A method of performing a motion-compensated injection of a material, comprising:
providing a handheld injector comprising a hollow shaft, the hollow shaft having a distal end and being configured to deliver a material to a target location of tissue of a subject;
providing an optical coherence tomography-based optical detection system comprising:
an optical fiber with a distal end at a fixed distance from the distal end of the hollow shaft, wherein the optical fiber is adjacent but not concentric to the hollow shaft, and
an optical sensor;
monitoring, with the optical detection system, a distance between the distal end of the optical fiber and the target area for the motion-compensated injection;
inserting the hollow shaft into the tissue while controlling the position of the distal end of the hollow shaft based on a closed-loop proportional-integral-derivative control algorithm to compensate for deformation of the tissue during insertion of the hollow shaft;
controlling a position of the hollow shaft along a longitudinal axis of the hollow shaft to reduce a change in the distance between the distal end of the optical fiber and the target location; and
injecting the material.

21. The method of performing the motion-compensated injection of the material according to claim 20, further comprising imaging the target area using the optical detection system after injecting the material.

22. The method of performing the motion-compensated injection of the material according to claim 20, further comprising determining a position of the material after injecting the material.

23. The method of performing the motion-compensated injection of the material according to claim 20, wherein the controlling of the position of the hollow shaft is performed at least during the injection of the material.

24. The method of performing the motion-compensated injection of the material according to claim 20, wherein the optical detection system uses common-path optical coherence tomography.

* * * * *